(12) United States Patent
Wang

(10) Patent No.: US 8,015,855 B2
(45) Date of Patent: Sep. 13, 2011

(54) EXHAUST GAS SENSOR

(75) Inventor: Liming Wang, Easley, SC (US)

(73) Assignee: Robert Bosch GmbH, Stuttgart (DE)

( * ) Notice: Subject to any disclaimer, the term of this patent is extended or adjusted under 35 U.S.C. 154(b) by 157 days.

(21) Appl. No.: 12/527,226

(22) PCT Filed: Oct. 3, 2007

(86) PCT No.: PCT/US2007/080242
§ 371 (c)(1),
(2), (4) Date: Aug. 14, 2009

(87) PCT Pub. No.: WO2008/103192
PCT Pub. Date: Aug. 28, 2008

(65) Prior Publication Data
US 2010/0064769 A1 Mar. 18, 2010

Related U.S. Application Data

(60) Provisional application No. 60/891,259, filed on Feb. 23, 2007.

(51) Int. Cl.
*G01N 7/00* (2006.01)
*G01N 7/06* (2006.01)
(52) U.S. Cl. ........................ 73/23.32; 73/31.05; 204/424
(58) Field of Classification Search .......... 439/101–107; 204/424, 425, 427; 73/23.32, 31.05
See application file for complete search history.

(56) References Cited

U.S. PATENT DOCUMENTS

| | | | |
|---|---|---|---|
| 4,178,798 A | 12/1979 | Wessel | |
| 4,222,026 A | 9/1980 | Heiney, III et al. | |
| 4,223,293 A | 9/1980 | Springer et al. | |
| 4,230,930 A | 10/1980 | Chang et al. | |
| 4,284,487 A | 8/1981 | Barnes et al. | |
| 4,440,621 A * | 4/1984 | Kitahara et al. | 204/406 |
| 4,479,868 A | 10/1984 | McIntyre et al. | |
| 4,629,549 A * | 12/1986 | Kojima et al. | 204/406 |

(Continued)

FOREIGN PATENT DOCUMENTS

| | | |
|---|---|---|
| EP | 1391724 | 2/2004 |
| WO | 2004086023 | 10/2004 |

OTHER PUBLICATIONS

PCT/US2007/080242 International Search Report and Written Opinion, dated Mar. 26, 2008, 10 pages.

High Temp Metals, NI 200/201 Technical Data, webpages retrieved Feb. 19, 2007 from http://www.hightempmetals.com/techdata/hitempNi200data.php, 2 pages.

Introduction to Thermoelectrics, webpages retrieved Feb. 19, 2007 from http://www.thermoelectrics.com/introduction.htm, 5 pages.

(Continued)

*Primary Examiner* — Lisa Caputo
*Assistant Examiner* — Punam Roy
(74) *Attorney, Agent, or Firm* — Michael Best & Friedrich LLP

(57) ABSTRACT

A method of manufacturing an exhaust gas sensor allows the manufacturer to selectively control the air-voltage range of the manufactured sensor between a first air-voltage range and a second air-voltage range. The sensor includes a signal wire and a ground wire. The method includes using a high nickel alloy for both of the signal wire and the ground wire to manufacture a sensor in the first air-voltage range, and using a high nickel alloy for only one of the signal wire and the ground wire to manufacture a sensor in the second air-voltage range. The air-voltage ranges are those associated with a lean-application normalized air/fuel ratio of $\lambda > 1$.

29 Claims, 4 Drawing Sheets

U.S. PATENT DOCUMENTS

| | | | | |
|---|---|---|---|---|
| 4,784,728 | A | * | 11/1988 | Capone .................. 205/785 |
| 5,279,154 | A | | 1/1994 | Vavra et al. |
| 5,329,806 | A | * | 7/1994 | McClanahan et al. ....... 73/31.05 |
| 6,551,498 | B2 | | 4/2003 | Nelson |
| 6,613,208 | B2 | | 9/2003 | Vargo et al. |
| 2005/0224347 | A1 | | 10/2005 | Hahn et al. |
| 2007/0012087 | A1 | | 1/2007 | Ruth et al. |

OTHER PUBLICATIONS

Introduction to thermoelectricity, webpages retrieved Feb. 19, 2007 from http://www.chem.cornell.edu/fjd3/thermo/intro.html, 4 pages.

P.A. Inc., Nickel 200/201, webpage retrieved Feb. 19, 2007 from http://www.painc.com/nickel_200_201.htm, 1 pages.

Alloy Wire International Ltd, Nickel 200, webpage retrieved Feb. 19, 2007 from http://www.alloywire.com/nickel_200.html.

* cited by examiner

EXHAUST GAS SENSOR

RELATED APPLICATIONS

This application claims priority to U.S. Provisional Patent Application No. 60/891,259 filed Feb. 23, 2007, the entire content of which is hereby incorporated by reference.

BACKGROUND

The present invention relates to exhaust gas sensors, and more particularly to exhaust gas sensors used for lean air/fuel ratio applications.

Exhaust gas sensors are well known for use in automotive and other industries. Certain exhaust gas sensors, such as sensors used in high performance race cars, ovens, boilers, and diesel vehicles, must be capable of performing well in lean air/fuel ratio applications where the normalized air/fuel ratio, $\lambda$, is greater than 1. $\lambda$ is determined based on the following equation:

$$\lambda = \frac{(A/F)_{actual}}{(A/F)_{ideal}}$$

where: $A/F$ = Air/fuel ratio

These lean-application exhaust gas sensors typically have a low air-voltage, which is the voltage measured between the signal wire lead and the ground lead when the sensor is operating in an air-only atmosphere (i.e., no fuel is present). The air-voltage can be considered an indicator of the sensor's sensitivity. Three known and commonly requested air-voltage ranges for lean-applications sensors are about −8.5 mV to about −12 mV, about −12 mV to about −15 mV, and about −15 mV to about −18 mV.

FIG. 1 illustrates a prior art lean-application exhaust gas sensor 10. The illustrated prior art sensor is known as a 3-wire sensor because it includes one signal wire 14 and two heater wires 18 (only one shown in FIG. 1) housed in the sensor 10. There is no ground wire incorporated in the sensor 10. As shown in FIG. 2, the sensor 10 is connected to a wire harness having two heater leads 22 electrically coupled to the respective heater wires 18, one signal lead 26 electrically coupled to the signal wire 14, and a ground lead 30 that is welded to a metal cap 34, thereby grounding the ground lead 30 via the electrical connection with the metallic housing 38, the sleeve 42, and the seal ring 46 (see FIG. 1) of the sensor 10. The ground electrode of the ceramic sensor element 54 is also connected to the housing 38 as the ground. The air-voltage of the sensor 10 is measured by measuring the voltage across the signal lead 26 and the ground lead 30.

FIG. 3 illustrates the circuit model for the sensor 10. Reference numeral 50 represents the signal supplied by the signal wire 14, reference numeral 54 represents the ceramic sensor element, and reference numeral 58 represents the signal supplied by the ground lead 30. The air-voltage is the voltage measured between the positive and negative terminals shown in the circuit model when the sensor 10 is in air with no fuel present.

SUMMARY

It has been difficult to control the manufacture of lean-application sensors so that the sensors can be selectively manufactured to fall into a desired air-voltage range. Instead, the lean-application sensors are typically manufactured with the same components using the same process, and then only upon testing can it be determined into which air-voltage range the sensor falls (e.g., −8.5 mV to −12 mV, −12 mV to −15 mV, or −15 mV to −18 mV).

While it is known that slightly hotter temperatures created by the heater, and slightly lower masses of the ceramic sensor element for thimble-type lean-application sensors can result in sensors having lower air-voltages, these variables are difficult and costly to control. Therefore, sensor manufacturers have been forced to assemble the sensor and test it upon completion to determine the air-voltage. This "build-and-test" process leads to manufacturing quantity and inventory problems. Specifically, if a customer requests a certain number of lean-application sensors in the −12 mV to −15 mV air-voltage range, the manufacturer will have to build and test many more sensors than the customer desires because numerous of the manufactured sensors will test into the −8.5 mV to −12 mV air-voltage range, which does not meet the customer's specifications. Eventually, when the number of lean-application sensors in the −12 to −15 mV air-voltage range requested by the customer has been manufactured, the manufacturer is left with an inventory of sensors in the −8.5 mV to −12 mV range. This leads to excess inventory that must be held until another customer requests sensors in the −8.5 mV to −12 mV air-voltage range. It also causes problems in determining the number of components and the amount of time it will take to fill a customer's order.

The present invention provides a new construction and assembly process for lean-application exhaust gas sensors. The inventive construction and process enables a manufacturer to more accurately selectively control the air-voltage range of a lean-application sensor based on material selection of various components, thereby enabling the manufacturer to make lean-applications sensors that will test into the desired air-voltage range at a much higher percentage than the purely random arrangement observed in the prior art. Manufacturing and inventory costs are greatly reduced.

In one embodiment, the invention provides a lean-application exhaust gas sensor having a sensor element, a signal wire electrically coupled to the sensor element and configured for connection to a wire harness, and a ground wire configured for connection to a wire harness. At least one of the signal wire and the ground wire are made of a high nickel alloy.

In another embodiment the invention provides a method of manufacturing an exhaust gas sensor so as to selectively control the air-voltage range of the manufactured sensor between a first air-voltage range and a second air-voltage range. The sensor includes a signal wire and a ground wire. The method includes using a high nickel alloy for both of the signal wire and the ground wire to manufacture a sensor in the first air-voltage range, and using a high nickel alloy for only one of the signal wire and the ground wire to manufacture a sensor in the second air-voltage range.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
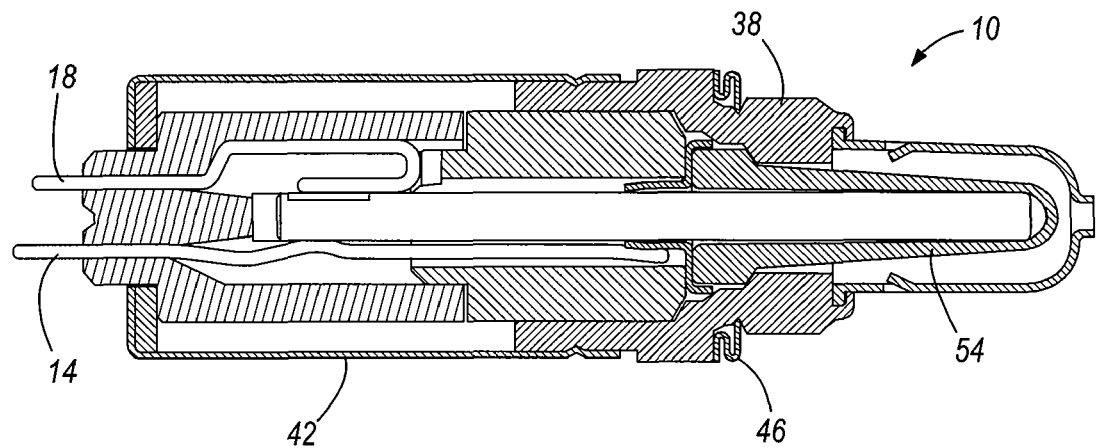
FIG. 1 is a section view of a prior art lean-application sensor.
Figure 2:
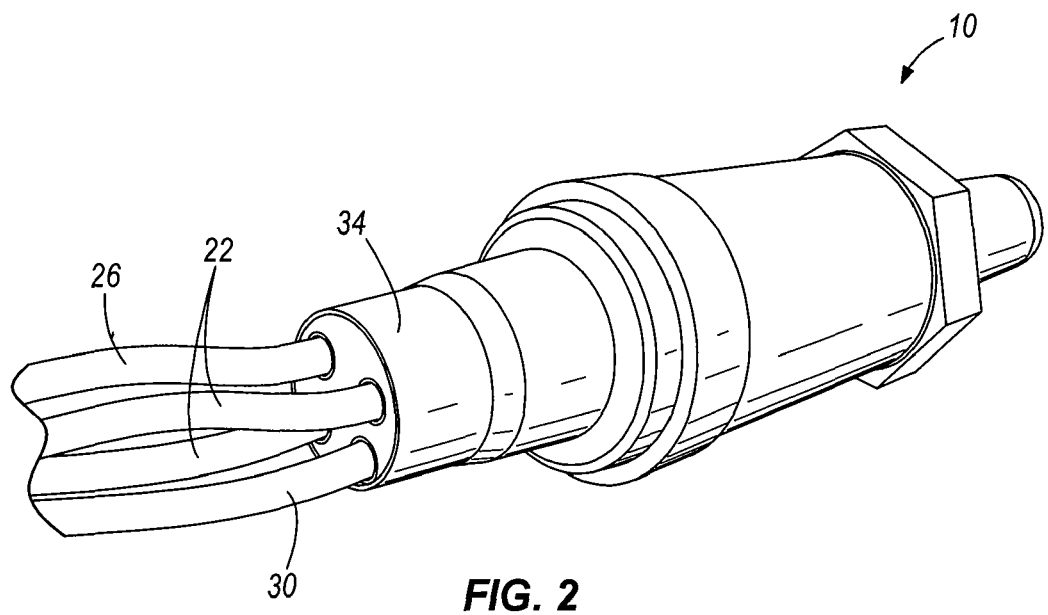
FIG. 2 is a rear perspective view of the sensor of FIG. 1 coupled with a wire harness.
Figure 3:
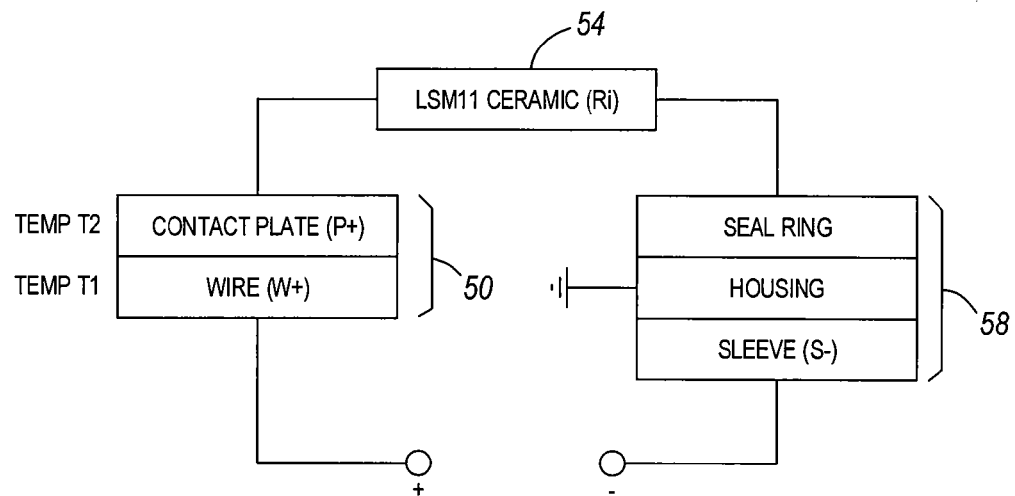
FIG. 3 is a circuit diagram for the sensor of FIG. 1.
Figure 4:
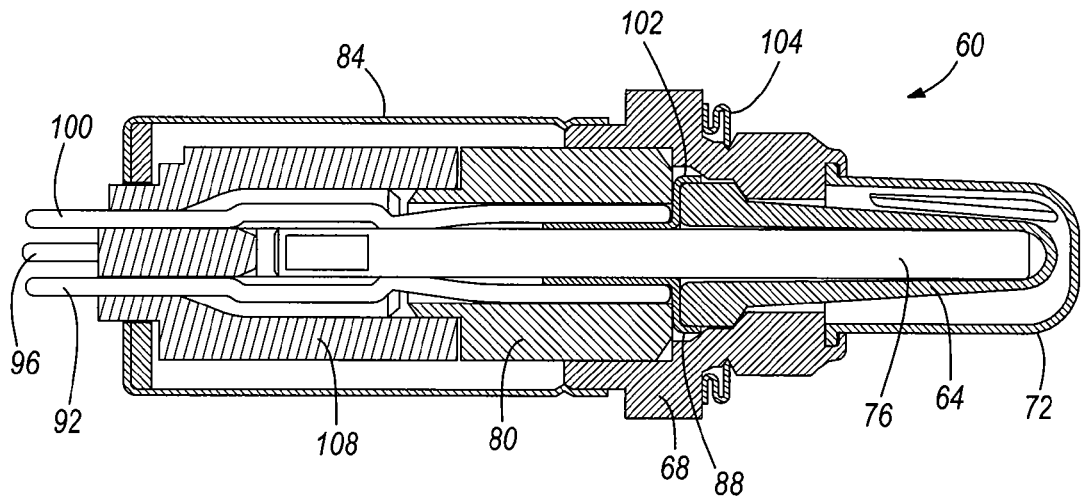
FIG. 4 is section view of a lean-application sensor embodying the present invention.
Figure 7:
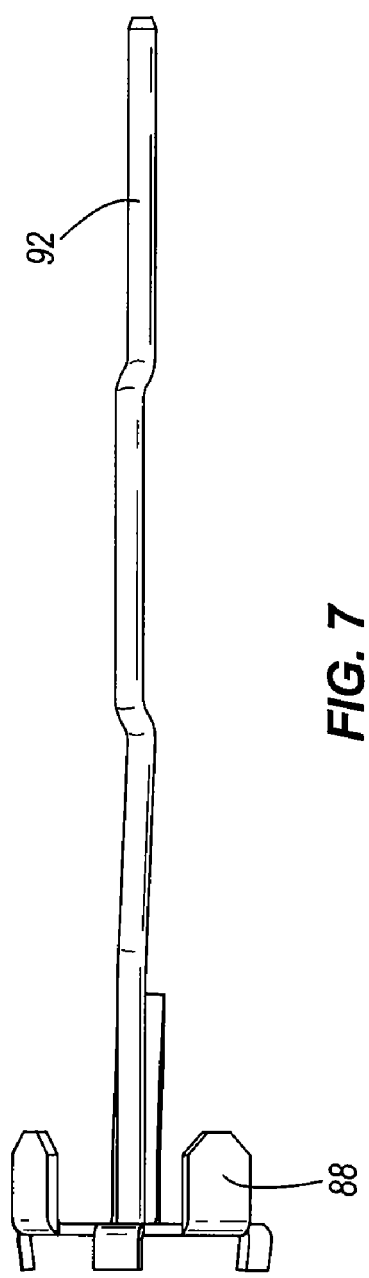
FIG. 7 is a side view of a signal wire and signal contact plate of the sensor of FIG. 4.

FIG. 4 illustrates a lean-application sensor 60 embodying the present invention. The sensor 60 is a thimble-type sensor having a ceramic sensor element 64 supported in a metallic housing 68. A protection tube 72 is coupled to the housing 68 to protect the sensor element 64 from exhaust gases. The protection tube 72 can have various configurations and can include holes formed in different ways and positioned in different locations, as is understood in the art. A heater 76 extends into the sensor element 64, as is known in the art. An insulating bushing or spacer 80 is housed at least partially within the housing 68 and insulates the heater 76 from the housing 68 and from a sleeve 84 coupled to the housing 68. A contact plate 88 is sandwiched between the sensor element 64 and the bushing 80 and electrically connects the sensor element 64 to a signal wire 92, as is commonly understood in the art. In the illustrated embodiment, the contact plate 88 and the signal wire 92 are coupled together as shown in FIG. 7. Two heater wires 96 (only one is shown in FIG. 4) are electrically coupled to the heater 76 to provide power to the heater 76.

Figure 5:
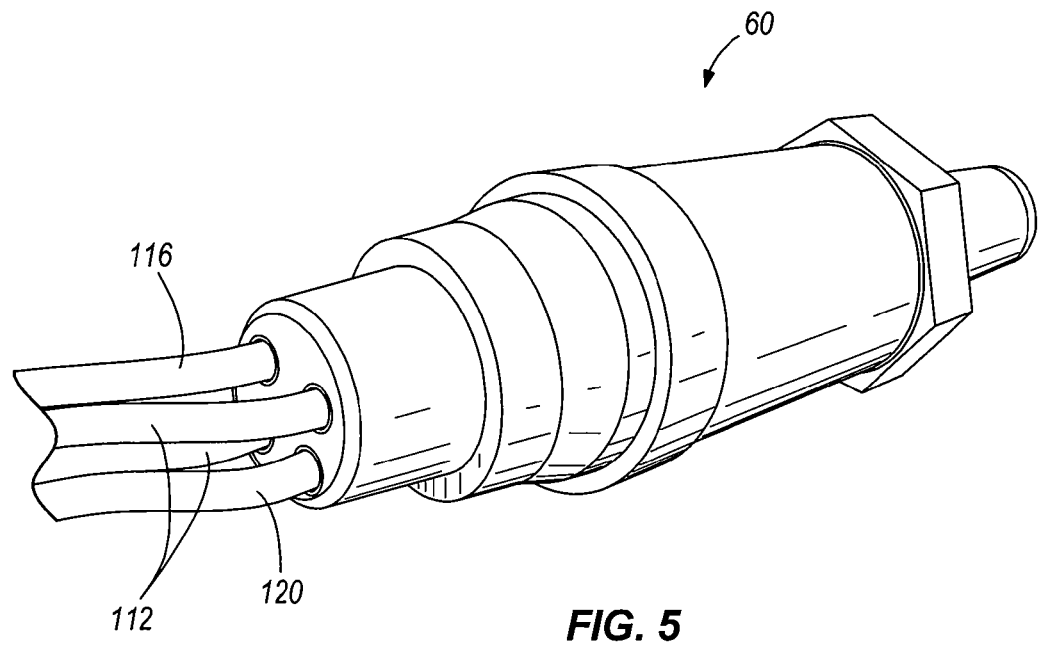
FIG. 5 is a rear perspective view of the sensor of FIG. 4 coupled with a wire harness.
Figure 8:
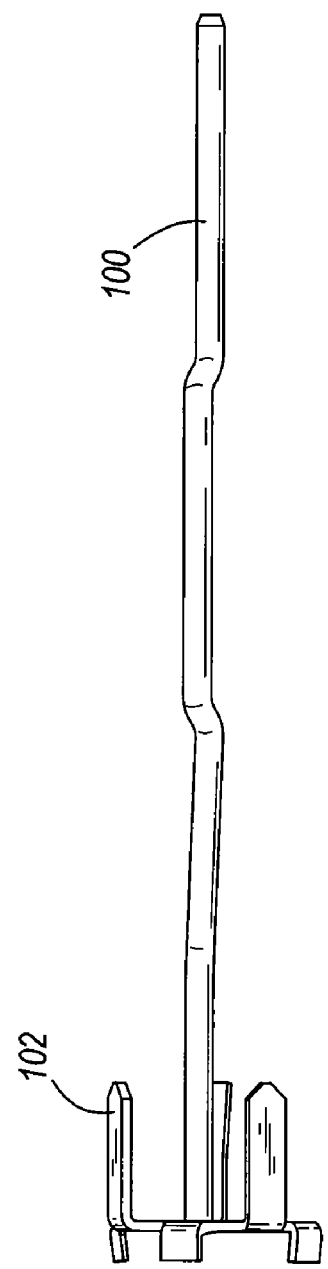
FIG. 8 is a side view of a ground wire and ground contact plate of the sensor of FIG. 4.

Unlike the prior art lean-application sensor 10, the lean-application sensor 60 of the present invention also includes a ground wire 100 incorporated directly into the sensor, rendering the sensor 60 a 4-wire sensor. The ground wire 100 is electrically connected through a ground contact plate 102 to the ground electrode of the sensor element 64 as well as to the housing 68, the sleeve 84, and a seal ring 104 supported on the housing 68, thereby functioning as an additional ground in parallel with the structure of the housing 68, the sleeve 84, and the seal ring 104. In the illustrated embodiment, the contact plate 102 and the ground wire 100 are coupled together as shown in FIG. 8. The signal wire 92, the heater wires 96, and the ground wire 100 extend through respective bores in another bushing or spacer 108 supported within the sleeve 84, and out from an end of the bushing 108 and sleeve 84 to connect to a wire harness having two heater leads 112, a signal lead 116, and a ground lead 120 (see FIG. 5). For more detail on the general construction of the sensor 60, including the construction of the signal and ground wires, the contact plates, the bushings, etc., reference is made to somewhat similar sensor constructions in US Published Application No. 2005/0224347 A1, published on Oct. 13, 2005, the entire of content of which is hereby incorporated by reference. Note that the sensor disclosed in the '347 application is not a lean-application sensor, nor is it a heated 4-wire sensor, but is rather incorporated to describe the general construction and assembly of common features.

Figure 6:
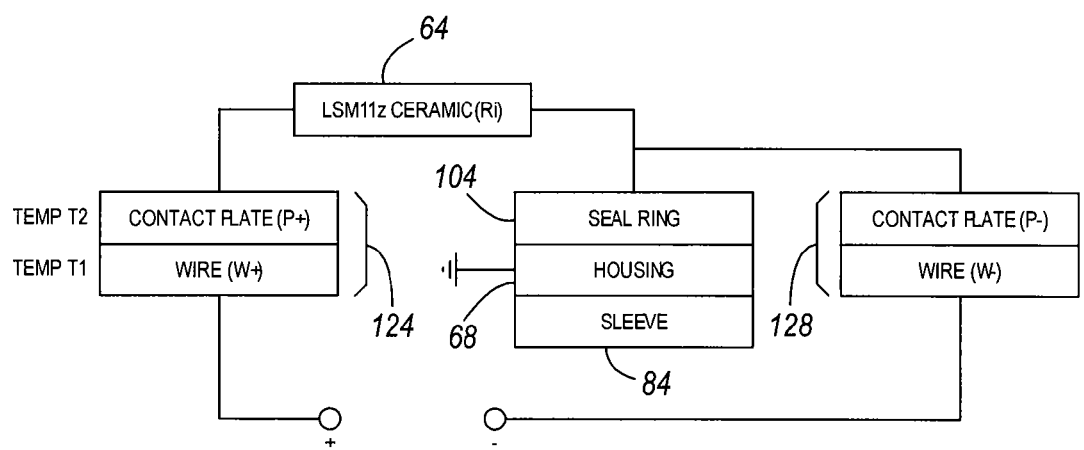
FIG. 6 is a circuit diagram for the sensor of FIG. 4.

FIG. 6 illustrates the circuit model for the sensor 60. Reference numeral 124 represents the signal supplied by the signal wire 92, and reference numeral 128 represents the signal supplied by the ground wire 100 in parallel to the ground structure of the housing 68, the sleeve 84, and the seal ring 104. The air-voltage is the voltage measured between the positive and negative terminals shown in the circuit model when the sensor 60 is in air with no fuel present.

While 4-wire sensors (i.e., heated sensors incorporating a ground wire) are known in the exhaust gas sensor art, most lean-application sensors, or sensors designed to operate in conditions where the normalized air/fuel ratio is represented by $\lambda > 1$, have measured air-voltages ranging from about −8.5 mV to about −18 mV, and have typically been 3-wire sensors like the prior art sensor 10. As discussed above in the Summary, it has proven difficult or impossible to selectively manufacture lean-application sensors that generally fall within a desired one of two or more commonly-requested air-voltage ranges (e.g., from about −8.5 mV to about −12 mV, or from about −12 mV to about −15 mV).

The inventive sensor 60 provides a lean-application sensor that can be selectively constructed to achieve desired air-voltages falling within commonly requested air-voltage ranges. This helps eliminate the added inventory and manufacturing costs associated with the prior art technique of simply building and testing the sensors 10 to randomly achieve various air-voltages without any control or selectability over the air-voltages achieved.

One aspect of the invention lies in the application of the "thermocouple effect" or the "Seebeck effect" to the sensor 60. This scientific principle is based on the understanding that any two different materials or alloys, when electrically coupled together with a temperature difference between them, will create a voltage potential between the two materials. When applied to the sensor 60, it has been found that the air-voltage values can be generally predicted to fall within one of two or more desirable air-voltage ranges (e.g., from about −8.5 mV to about −12 mV, or from about −12 mV to about −15 mV) based on the combination of materials selected for use as the signal wire 92 and the ground wire 100.

More specifically, the prior art sensor 10 utilized a signal wire made of a Nickel 200 high nickel alloy containing about 99.6% nickel by weight (sometimes referred to as a pure nickel alloy due to its nickel content of greater than ninety-nine weight percent), and a signal contact plate made of an alloy containing about 21% nickel by weight. The air-voltage of the prior art sensor 10 was dictated in part by the ground materials of the seal ring, the housing, and the sleeve, each of which were made of various stainless steel compositions. Because the signal wire conventionally used in 3-wire, lean-application exhaust gas sensors is a high nickel or pure nickel alloy, and because the ground of the prior art sensor was dictated by the standard external structural components of the sensor 10, variation of the chemistries of these components was not a practical manner of attempting to selectively control the air-voltage. Therefore, taking advantage of the Seebeck effect in an attempt to control the air-voltage of the sensor 10 was not a readily apparent or feasible option.

However, the inventive sensor 60 incorporates a separate ground wire 100, thereby introducing another component into the circuit. The addition of the ground wire 100 provides more flexibility because there are now more components that can be readily and easily varied between a number of materials or chemistries to take advantage of the Seebeck effect, and therefore help control the air-voltage of the sensor 60. Specifically, the materials for the signal wire 92 and/or the ground wire 100 can be selectively chosen to achieve a sensor 60 that can be produced to more selectively achieve a desired air-voltage, or more specifically to fall within one of two or more desired air-voltage ranges (e.g., from about −8.5 mV to about −12 mV, or from about −12 mV to about −15 mV) with greatly increased predictability.

Test results for one matrix of materials is set forth below in Table 1.

TABLE 1

| Sensor Construction | Signal Wire Material | Ground Wire Material | Air-Voltage Range |
|---|---|---|---|
| 1 | Nickel 201 (Approx. 99.6 wt % Ni) | Ni2b2 (Approx. 78 wt % Ni) | Approx. 84% at −12 mV to −15 mv Approx. 16% at −8.5 mV to −12 mv |
| 2 | Nickel 201 (Approx. 99.6 wt % Ni) | Nickel 201 (Approx. 99.6 wt % Ni) | Approx. 92% at −8.5 mV to −12 mv Approx. 8% above −8.5 mV-rejected |

The above table illustrates how the choice of materials for the signal wire 92 and the ground wire 100, without other process changes, significantly impacts the air-voltage range of the manufactured sensors 60. Specifically, should a customer request sensors falling within the −12 mV to −15 mv air-voltage range, Sensor Construction 1 can be chosen and will result in about eighty-four percent of the manufactured sensors falling into the customer's requested specifications. This is a significant improvement over the prior art sensor 10, of which the as-manufactured air-voltage cannot be controlled. Likewise, should a customer request sensors falling within the −8.5 mV to −12 mv air-voltage range, Sensor Construction 2 can be chosen and will result in about ninety-two percent of the manufactured sensors falling into the customer's requested specifications.

The sensor 60 can also be manufactured with signal wires and ground wires made from other medium nickel alloys (i.e., nickel alloys containing between about sixty and about eighty weight percent nickel) or high nickel alloys (i.e., nickel alloys containing more than eighty-five weight percent nickel, and including pure nickel alloys containing more than ninety-nine weight percent nickel), such as Nickel 200 for example. However, Nickel 201 has been found to provide advantages over Nickel 200 due to an increased stability of the sensor 60 achieved with the use of Nickel 201. Nickel 201 has a maximum carbon content of about 0.02 percent by weight, while Nickel 200 has a maximum carbon content of about 0.15 percent by weight. The lower carbon content of Nickel 201 renders it more stable at temperatures above 315 degrees Celsius, at or above which most of the lean-application sensors are operated, because there is less carbon to precipitate or diffuse out of the wires at these high temperatures. Likewise, other nickel alloys used can also be selected, if desired, to have a maximum carbon content of less than about 0.15 percent by weight to improve functional stability.

Modeling can be performed to select other materials that will meet the desired air-voltage ranges. Specifically, the air-voltage can be modeled based on the following equation in view of the circuit model shown in FIG. 6.

$$AirVoltage = \int_{T_{low}}^{T_{high}} S_{Signal} dt + \int_{T_{high}}^{T_{low}} S_{Ground} dt$$

where:
$S_{Signal}$ is the Seebeck coefficient for the signal wire 92
$S_{Ground}$ is the Seebeck coefficient for the ground wire 100
T is the temperature furthermore, the Seebeck coefficient is represented as:

$$S = \frac{dV}{dT} \approx -\frac{\pi^2 k^2 T}{2eE_{FO}} = aT$$

where:
k is the Boltzmann Constant ($1.380658 \times 10^{-23}$ JK$^{-1}$)
T is the temperature in Kelvin
e is the elementary charge ($1.6022 \times 10^{-19}$ C)
$E_{FO}$ is the Fermi Energy at 0 degrees Kelvin in electron volts Substituting yields:

$$AirVoltage = \frac{1}{2}(a_{Signal} - a_{Ground})(T_{high}^2 - T_{low}^2)$$

The ability to vary materials for the signal wire 92 and the ground wire 100 provides the ability to better achieve control over air-voltage selectability. Further improvements on the achieved air-voltage range percentages can be obtained by subsequent fine tuning of the other controllable variables in the sensor 60, including the heater 76 temperature and the mass of the ceramic sensor element 64. However, even without further fine tuning, the addition of a ground wire 100, and the use of different materials for the ground wire 100 and the signal wire 92 to control the resulting air-voltage characteristic of the sensor 60 provides a significant improvement over the prior art sensor 10, with which there was no practical or economical method of selectively controlling the resulting air-voltage characteristic. Furthermore, the addition of the ground wire 100 to the lean-application sensor 60 enables some commonization and harmonization of parts and manufacturing processes with other 4-wire sensors manufactured for other applications (e.g., non-lean-application sensors).

Various features of the invention are set forth in the following claims.

What is claimed is:
1. A lean-application exhaust gas sensor comprising:
a sensor element;
a signal wire electrically coupled to the sensor element and configured for connection to a wire harness; and
a ground wire configured for connection to a wire harness;
wherein the sensor is configured as a lean-application sensor for operation where the air/fuel ratio is represented by λ>1, where

$$\lambda = \frac{(A/F)_{actual}}{(A/F)_{ideal}} \text{ and } A/F = \text{air/fuel ratio;}$$

wherein the sensor defines an air-voltage measured between the signal wire and the ground wire, the air-voltage being in the range of about −8.5 mV to about −15 mV; and wherein at least one of the signal wire and the ground wire are made of a high nickel alloy.

2. The sensor of claim 1, wherein only the signal wire is made of a high nickel alloy, and wherein the ground wire is made of an alloy having a lower nickel content than the high nickel alloy.

3. The sensor of claim 2, wherein the air-voltage is in the range of about −12 mV to about −15 mV.

4. The sensor of claim 1, wherein both of the signal wire and the ground wire are made of a high nickel alloy.

5. The sensor of claim 4, wherein the air-voltage is in the range of about −8.5 mV to about −12 mV.

6. The sensor of claim 1, wherein the high nickel alloy contains more than eighty-five percent by weight nickel.

7. The sensor of claim 6, wherein the high nickel alloy contains more than ninety-nine percent by weight nickel.

8. The sensor of claim 1, wherein the high nickel alloy is Nickel 200.

9. The sensor of claim 1, wherein the high nickel alloy is Nickel 201.

10. A lean-application exhaust gas sensor comprising:
a sensor element;
a signal wire electrically coupled to the sensor element;
a ground wire;
a heater at least partially received in the sensor element;
first and second heater wires electrically coupled with the heater; and
a wire harness, the wire harness including
 first and second heater leads electrically coupled to the respective first and second heater wires;
 a signal lead electrically coupled to the signal wire; and
 a ground lead electrically coupled to the ground wire
wherein the sensor is configured as a lean-application sensor for operation where the air/fuel ratio is represented by λ>1, where $$\lambda = \frac{(A/F)_{actual}}{(A/F)_{ideal}} \text{ and } A/F = \text{air/fuel ratio;}$$

and
wherein at least one of the signal wire and the ground wire are made of a high nickel alloy.

11. The sensor of claim 10, wherein the sensor defines an air-voltage measured between the signal wire and the ground wire, the air-voltage being in the range of about −8.5 mV to about −15 mV.

12. The sensor of claim 10, wherein only the signal wire is made of a high nickel alloy, and wherein the ground wire is made of an alloy having a lower nickel content than the high nickel alloy.

13. The sensor of claim 12, wherein the sensor defines an air-voltage measured between the signal wire and the ground wire, the air-voltage being in the range of about −12 mV to about −15 mV.

14. The sensor of claim 10, wherein both of the signal wire and the ground wire are made of a high nickel alloy.

15. The sensor of claim 14, wherein the sensor defines an air-voltage measured between the signal wire and the ground wire, the air-voltage being in the range of about −8.5 mV to about −12 mV.

16. The sensor of claim 10, wherein the high nickel alloy contains more than eighty-five percent by weight nickel.

17. The sensor of claim 16, wherein the high nickel alloy contains more than ninety-nine percent by weight nickel.

18. The sensor of claim 10, wherein the high nickel alloy is Nickel 200.

19. The sensor of claim 10, wherein the high nickel alloy is Nickel 201.

20. A method of manufacturing an exhaust gas sensor so as to selectively control an air-voltage range of the manufactured sensor between a first air-voltage range and a second air-voltage range, the sensor including a signal wire and a ground wire, the method comprising:
determining which of the first air-voltage range and the second air-voltage range the manufactured sensor is desired to have; and
if the first air-voltage range is desired for the manufactured sensor, using a high nickel alloy for both of the signal wire and the ground wire to manufacture a sensor in the first air-voltage range; and
if the second air-voltage range is desired for the manufactured sensor, using a high nickel alloy for only one of the signal wire and the ground wire to manufacture a sensor in the second air-voltage range.

21. The method of claim 20, wherein the first air-voltage range is about −8.5 mV to about −12 mV, and wherein the second air-voltage range is about −12 mV to about −15 mV.

22. The method of claim 20, wherein the high nickel alloy contains more than eighty-five percent by weight nickel.

23. The method of claim 20, wherein the high nickel alloy contains more than ninety-nine percent by weight nickel.

24. The method of claim 20, wherein the high nickel alloy is Nickel 200.

25. The method of claim 20, wherein the high nickel alloy is Nickel 201.

26. The method of claim 20, wherein using a high nickel alloy for only one of the signal wire and the ground wire includes using a high nickel alloy for only the signal wire.

27. The method of claim 20, wherein each of the first and second air-voltage ranges defines air-voltage ranges for use with sensors operable in applications where the air/fuel ratio is represented by λ>1, where $$\lambda = \frac{(A/F)_{actual}}{(A/F)_{ideal}} \text{ and } A/F = \text{air/fuel ratio.}$$

28. The method of claim 20, further comprising:
providing a wire harness including a signal wire lead and a ground wire lead;
electrically coupling the signal wire lead to the signal wire; and
electrically coupling the ground wire lead to the ground wire.

29. The method of claim 28, wherein the wire harness further includes first and second heater wire leads, the method further comprising:
providing a heater including first and second heater wires; and
electrically coupling the first and second heater wire leads to the respective first and second heater wires.

* * * * *